United States Patent [19]
Raskas

[11] Patent Number: 6,157,442
[45] Date of Patent: Dec. 5, 2000

[54] MICRO OPTICAL FIBER SENSOR DEVICE

[75] Inventor: Eric J. Raskas, St. Louis, Mo.

[73] Assignee: MicroSense International LLC, St. Louis, Mo.

[21] Appl. No.: 09/100,295

[22] Filed: Jun. 19, 1998

[51] Int. Cl.[7] ................................................. G01N 33/48
[52] U.S. Cl. .............................. 356/39; 356/40; 356/317
[58] Field of Search .............................. 356/39, 317, 320, 356/40

[56] References Cited

U.S. PATENT DOCUMENTS

| | | | |
|---|---|---|---|
| 5,341,805 | 8/1994 | Stavridi et al. | 128/633 |
| 5,361,314 | 11/1994 | Kopelman et al. | 385/12 |
| 5,398,681 | 3/1995 | Kupershmidt | 128/633 |
| 5,448,992 | 9/1995 | Kupershmidt | 128/633 |
| 5,529,755 | 6/1996 | Higashio et al. | 422/82.09 |
| 5,533,509 | 7/1996 | Koashi et al. | 128/633 |
| 5,553,613 | 9/1996 | Parker | 128/633 |
| 5,553,616 | 9/1996 | Ham et al. | 128/633 |
| 5,617,852 | 4/1997 | MacGregor | 128/633 |
| 5,627,922 | 5/1997 | Kopelman et al. | 385/12 |

OTHER PUBLICATIONS

Analytical Properties and Sensor Size Effects of a Micrometer–Sized Optical Fiber Glucose Biosensor, Zeev Rosenzweig and Raoul Kopelman, Analytical Chemistry, vol. 68, No. 8, Apr. 15, 1996, pp. 1408–1413.

Dermal Interstitial Glucose as an Indicator of Ambient Glycemia, F. John Service, Peter C. O'Brien, Steven D. Wise, Sheryl Ness, Suzanne M. LeBlanc, Diabetes Care, vol. 20, No. 9, Sep. 1997, pp. 1426–1429.

Primary Examiner—Frank G. Font
Assistant Examiner—Reginald A. Ratliff
Attorney, Agent, or Firm—Gregory E. Upchurch; Dennis J M Donahue, III; Thompson Coburn LLP

[57] ABSTRACT

A sensor device for measuring a concentration of a substance within a sample comprises a sensor comprising an optical fiber portion having a first end and a second end, the second end having a tip portion attached thereto and an active material incorporated within the tip portion, the tip portion adapted to be inserted into a sample, the active material capable of interacting with a substance within a sample, a light source coupled to the first end of the sensor for emitting a beam of light into and through the sensor and into a sample, the emitted beam of light having a wavelength and the active material interacting with a substance within a sample to change the wavelength of the emitted beam of light to produce a reflected beam of light and the sensor for transmitting the reflected beam of light out of the second end thereof, an optical detector for receiving the reflected beam of light from the second end of the sensor for producing a signal indicative of the reflected beam of light, and a processor for receiving the signal indicative of the reflected beam of light and for processing the signal to determine the concentration of a substance within a sample.

20 Claims, 3 Drawing Sheets

MICRO OPTICAL FIBER SENSOR DEVICE

BACKGROUND OF THE INVENTION

This invention relates generally to a sensor device and more particularly to a micro optical fiber sensor device which may be employed in a variety of sensor applications to monitor, sense, or measure a concentration of a material within a sample.

There are numerous applications in which a device is used to monitor or detect a concentration of material within a substance. For example, it may be required to know the concentration of a chemical in a sample of material such as knowing the concentration of sodium, calcium, or some other chemical composition in a sample. Monitoring or detecting a concentration of a substance typically requires a set up of relatively complex, sensitive, and expensive equipment or instrumentation. Sometimes space requirements make it difficult to use the set up of complex equipment and it would be advantageous to have equipment which has small dimensions and is easily transportable. Additionally, such complex equipment may not provide results which are of a high resolution.

One known and important application for monitoring a concentration of a material within a sample deals with checking blood glucose for diabetics. There are at least two known techniques for monitoring blood glucose levels in humans. The two techniques are invasive which involves extracting samples with the use of needles or syringes and noninvasive. Typically, for the invasive method, a patient employs a small lancet device which is used to prick or puncture a finger. Blood is then collected onto a strip which has incorporated therein a chemical reagent. The strip is then placed inside of a device that optically reads the chemical reaction of the blood on the strip and converts this to a blood glucose level. It has been found very important to control glucose levels in diabetics to reduce any complications associated with diabetes. Many samples or finger pricks may be required to be taken for analysis during the course of a day. Self monitoring of blood glucose by a patient is therefor very important in the treatment of diabetes. Since finger pricking or lancing is required for self monitoring levels of glucose in a patient, many patients avoid this because it is painful and inconvenient. Therefore, a less invasive procedure would be desirable. The other methods, which have been termed noninvasive, typically involve a devices which uses near infrared light to detect blood glucose levels. These devices measure a glucose concentration in blood or an organism's tissue by use of an optical device without the need to collect blood or fracturing a part of the organism's tissue. Although these devices use noninvasive methods, in that no blood is collected, none of these devices have been commercially accepted or viable.

The present invention is designed to obviate and overcome many of the disadvantages and shortcomings associated with the prior use of complex testing and monitoring equipment. Additionally, the present invention is simple to use, provides extremely quick results and high resolution, and is easily transportable. The present invention uses relatively inexpensive components which results in a commercially viable product. Further, the micro optical fiber sensor device of the present invention is relatively noninvasive since it does not require the drawing of blood and provides immediate results which does not require related blood processing such as centrifugation, storage, transportation, and other time consuming testing.

SUMMARY OF THE INVENTION

The present invention is a sensor device for measuring a concentration of a substance within a sample which comprises a sensor comprising an optical fiber portion having a first end and a second end, the second end having a tip portion attached thereto and an active material incorporated within the tip portion, the tip portion adapted to be inserted into a sample, the active material capable of interacting with a substance within a sample, a light source coupled to the first end of the sensor for emitting a beam of light into and through the sensor and into a sample, the emitted beam of light having a wavelength and the active material interacting with a substance within a sample to change the wavelength of the emitted beam of light to produce a reflected beam of light and the sensor for transmitting the reflected beam of light out of the second end thereof, means for receiving the reflected beam of light from the second end of the sensor for producing a signal indicative of the reflected beam of light, and a processor for receiving the signal indicative of the reflected beam of light and for processing the signal to determine the concentration of a substance within a sample.

Another example of the present invention is a sensor device for measuring a concentration of a substance within a sample which comprises a sensor comprising an optical fiber portion having a first end and a second end, the second end having a tip portion attached thereto and an active material incorporated within the tip portion, the tip portion adapted to be inserted into a sample, the active material capable of interacting with a substance within a sample, a light source for emitting a beam of light of a preselected wavelength with the light source being coupled to an optical device capable of transmitting the beam of light therethrough, the transmitted beam of light being directed into the first end of the sensor, through the sensor and out of the second end into a sample, the active material interacting with a substance within a sample to change the wavelength of the transmitted beam of light to produce a reflected beam of light and the sensor for transmitting the reflected beam of light from the second end, through the sensor, and out of the first end thereof, the optical device being further capable of reflecting the reflected beam of light, means for receiving the reflected beam of light which is reflected by the optical device for producing a signal indicative of the reflected beam of light; and a processor for receiving the signal indicative of the reflected beam of light and for processing the signal to determine the concentration of a substance within a sample.

A further example of the present invention is a sensor device for measuring a concentration of a substance within a sample which comprises a sensor comprising an optical fiber portion having a first end and a second end, the second end having a tip portion attached thereto and a first and a second active material incorporated within the tip portion, the tip portion adapted to be inserted into a sample, the first active material capable of interacting with a first substance within a sample and the second active material capable of interacting with a second substance within a sample, a light source coupled to the first end of the sensor for emitting a beam of light into and through the sensor and into a sample, the emitted beam of light having a wavelength and the first active material interacting with a first substance within a sample to change the wavelength of the emitted beam of light to produce a first reflected beam of light, the second active material interacting with a second substance within a sample to change the wavelength of the emitted beam of light to produce a second reflected beam of light, and the sensor for transmitting the first and second reflected beams of light out of the second end thereof, means for receiving the first and second reflected beams of light from the second end of the sensor for producing a first signal indicative of the first reflected beam of light and a second signal indicative of the second reflected beam of light, and a processor for receiving the first and second signals and for processing the first and second signals to determine the concentration of a first substance within a sample and the concentration of a second substance with a sample.

In light of the foregoing comments, it will be recognized that a principal object of the present invention is to provide an improved sensor device which is hand held, portable, and easy to operate.

Another object of the present invention is to provide a sensor device which has a tip portion of an extremely small size so that when it is inserted into a hand of a patient little or no sensation will be produced or detected.

A further object of the present invention is to provide a sensor device which is of simple construction and design and which can be easily employed with highly reliable results.

Another object of the present invention is to provide a sensor device which is accurate and provides readings in a short time span.

A still further object of the present invention is to provide a sensor device which is compact in design and is easily transportable for personal use.

These and other objects and advantages of the present invention will become apparent after considering the following detailed specification in conjunction with the accompanying drawings, wherein:

DETAILED DESCRIPTION OF THE PREFERRED EMBODIMENTS

Figure 1:
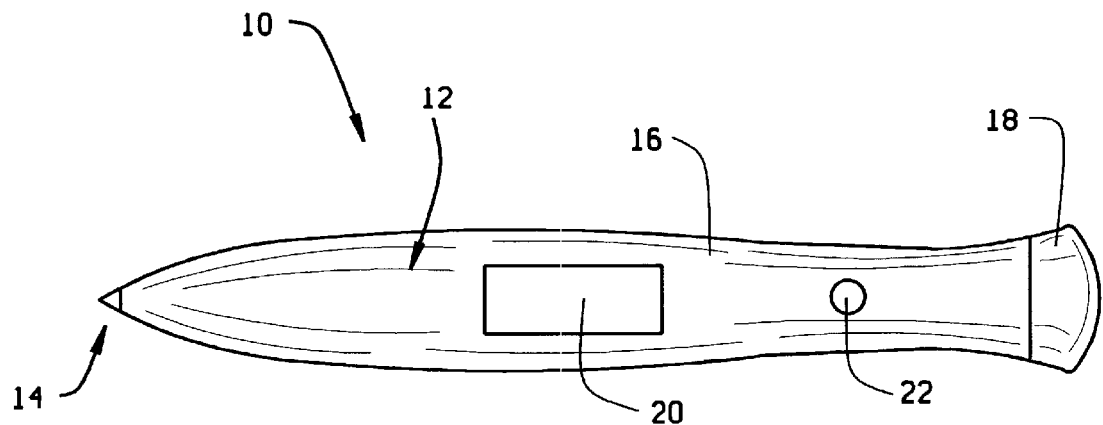
FIG. 1 is a perspective view of a micro optical fiber sensor device constructed according to the present invention.

Referring now to the drawings, wherein like numbers refer to like items, number 10 identifies a preferred embodiment of a micro optical fiber sensor device constructed according to the present invention. As illustrated in FIG. 1, the device 10 comprises a pencil or pen shaped body 12 which includes a tip portion 14, a central body portion 16, and an end cap 18. The central body portion 16 further includes a display device 20, such as an LED (light emitting diode) type display or an LCD type display, for displaying information. The end cap 18, which may be removable from the central body portion 16, is used to allow access into the interior of the central body portion 16. Batteries (not shown) can be inserted into the central body portion 16 to supply power to the device 10, as will be explained. The central body portion 16 may also include an ON/OFF switch 22 which may be used to operate the device 10. Other switches (not shown) may be incorporated into the central body portion 16 to further control the device 10. Additionally, the central body portion 16 houses electronic circuitry and other components which will be illustrated and explained in further detail herein. The device 10 is sized and shaped to be a hand held type device which is portable and preferably is the size and shape of a pencil or a pen.

Figure 2:
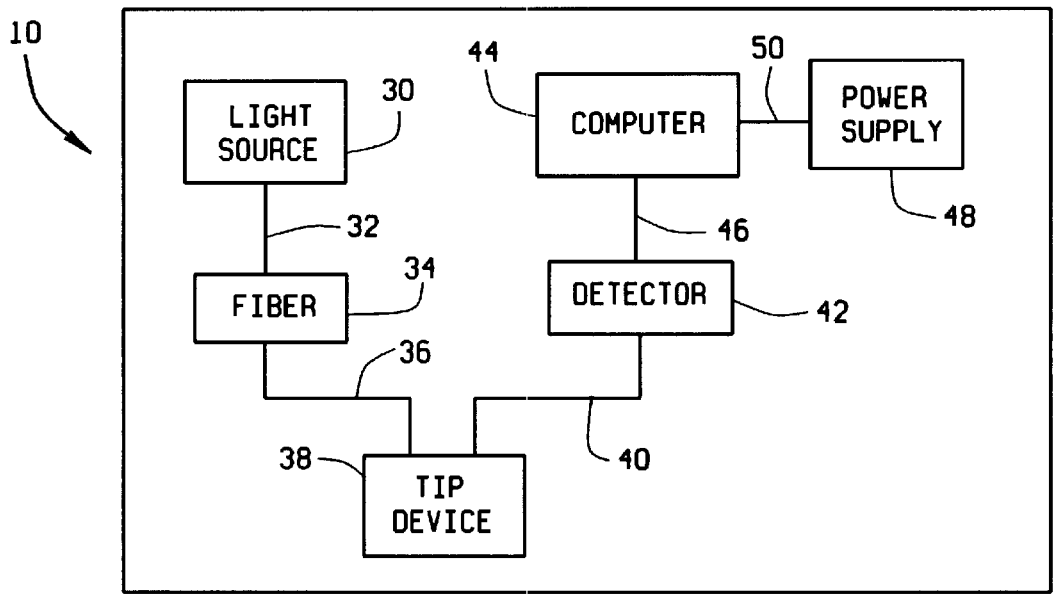
FIG. 2 is a block diagram of the micro optical fiber sensor device constructed according to the present invention.

With reference now to FIG. 2, a block diagram of the circuitry and components of the device 10 is shown. The device 10 includes a light source 30 which may be an LED, a laser, a laser diode, or other excitation source. The light source 30 is adapted to project a beam of light 32 into a section fiber optic 34. The fiber optic 34 transmits a beam of light 36 to a tip portion or device 38 which is part of the tip portion 14. The beam of light 36 passes through the tip device 38 and a reflected beam of light 40 can be reflected back from a sample (not shown) through the tip device 38 to a detector 42. The reflected beam of light 40 typically has a wavelength or a frequency which is different than the wavelength or frequency of the beam of light 36. The detector 42 is in turn connected to a computer 44 via an electrical connection such as a wire 46. The detector 42 provides electrical signals over the wire 46 to the computer 44. The computer 44 may consists of, by way of examples, a microprocessor, a microcontroller, an ASIC chip, or any other known equivalent device which is capable of processing electrical signals. The computer 44 is further operatively connected to a power supply 48, such as batteries, by a wire 50. The computer 44 may also connected to the display device 20, the switch 22, and the light source 30 although such connection is not illustrated in FIG. 2. Additionally, the computer 44 may also be connected to other switches (not shown) which may be provided with the device 10. In this manner, the additional switches are used to further control or operate other functions of the device 10.

Figure 3:
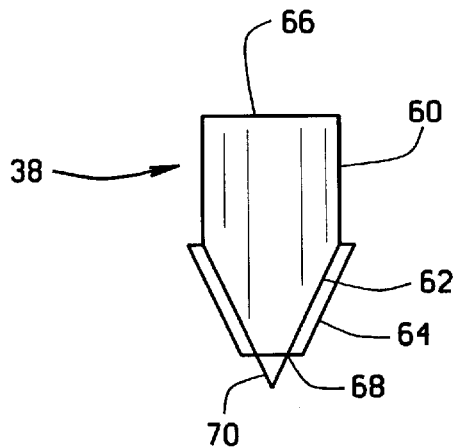
FIG. 3 is a perspective view of a tip portion of the micro optical fiber sensor device shown in FIG. 1.

The tip device 38 is shown in greater detail in FIG. 3 and is preferably a small device on the order of microns in diameter. The tip device 38 may be constructed as is disclosed in U.S. Pat. Nos. 5,361,314 and 5,627,922. In particular, the tip device 38 includes a non-tapered fiber optic portion 60 and a tapered fiber optic portion 62 which is coated with an opaque material 64. The tip device 38 further includes a first end 66 and a second end 68. The second end 68 further has a tip or portion 70 of material which is adhered thereto. The tip 70 is chemically treated which enables the tip 70 to interact with the sample to be detected. Properties of the sensor or tip device 38 may vary dependent upon the sample and the chemical or substance to be detected by the device 10. As constructed, the tip device 38 allows for the beam of light 36 to pass through the first end 66, the second end 68, and the tip portion 70 and the reflected beam 40 is allowed to pass through the tip portion 70, the second end 68, and the first end 66.

As indicated above, the tip device 38 is extremely small on the order of one-thousandth the width of a human hair and because of this size it can be inserted through gaps in most cells or through the membrane of a cell without damaging the cell. The tip 70 may be bathed in chemical coatings selected to react with biological compounds such as acid, calcium, oxygen, glucose, potassium, sodium, or any other material to be detected. The beam of light 36 which is transmitted through the tip device 38 glows with its brightness and color varying according to the concentration of the target chemical. The portion 70 is a photochemical sensor which is less than ten microns in diameter. Again, the portion 70 is small enough that it can pass through the membrane of a cell to monitor the concentration and nature of chemicals within the cell.

The tip device 38 may have specific chemical sensitivities based upon the properties of a dye matrix. A dye may be chemically activated by a different chemical compound which enables sensing of a specific chemical property within a sample or a substance. The tip device 38 provides for enhanced sensitivity, selectivity, and stability when detecting a concentration within a sample or substance. The tip portion or device 38 may comprise a biologically active compound that is immobilized in an environment that is optically reactive. Additionally, the biologically active compound can, in itself, be optically active. The sensor device 10 interacts with the substance or sample to detect a specific chemical or concentration within the substance.

Figure 4:
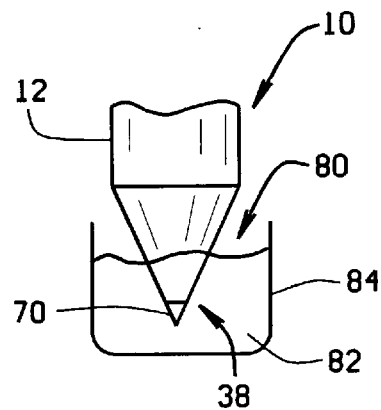
FIG. 4 is a schematic view of the micro optical fiber sensor device of the present invention being employed to sense a concentration in a sample.

With reference now to FIGS. 1, 2, and 4, the operation of the device 10 will be explained in detail. In order to operate the device 10, the on/off switch 22 is pressed to initialize the device 10. Once powered, the device 10 may be inserted into a sample 80 to test for a particular concentration of material within the sample 80. As shown in FIG. 4, the sample to be tested is a liquid 82 in a beaker 84. The tip portion 70 is inserted into the liquid 82 and at this point in time a beam of light, such as the beam of light 36, is transmitted into the liquid 82. With the tip portion 70 being in contact with the liquid 82, the liquid 82 reacts chemically with the tip portion 70 and the color of the chemical composing the sensor device 10 changes. As a result of this change, the color of the light reflected back into the tip portion 70 changes, such as reflected beam of light 40, as compared to the beam of light 36. The amount of this change can be quantified by the detector 42. Once quantified signals are provided to the computer 44 which performs a calculation to determine the concentration of the particular chemical being sensed and the result may be displayed in the display 20.

In further detail and again with reference to FIGS. 1, 2, and 4, once the device 10 is actuated by pressing the switch 22, the beam of light 32 is sent from the light source 30 through the fiber optic 34 which transmits the beam of light 36 through the tip device 38 into the liquid 82. The reflected beam of light 40 is reflected from the liquid 82 into the tip device 38 to the detector 42. The detector 42 provides signals to the computer 44 and the computer 44 determines the concentration of a particular chemical within the liquid 82. This process may be termed photochemical optical fiber sensing. Additionally, the chemical properties of the tip portion 70 of the sensor portion 14 may be changed to react with another chemical to detect some other chemical within a sample. Further, instead of changing the chemical properties of the tip portion 70, it may only be necessary to change the light source 30 to detect some other chemical within a sample.

Figure 5:
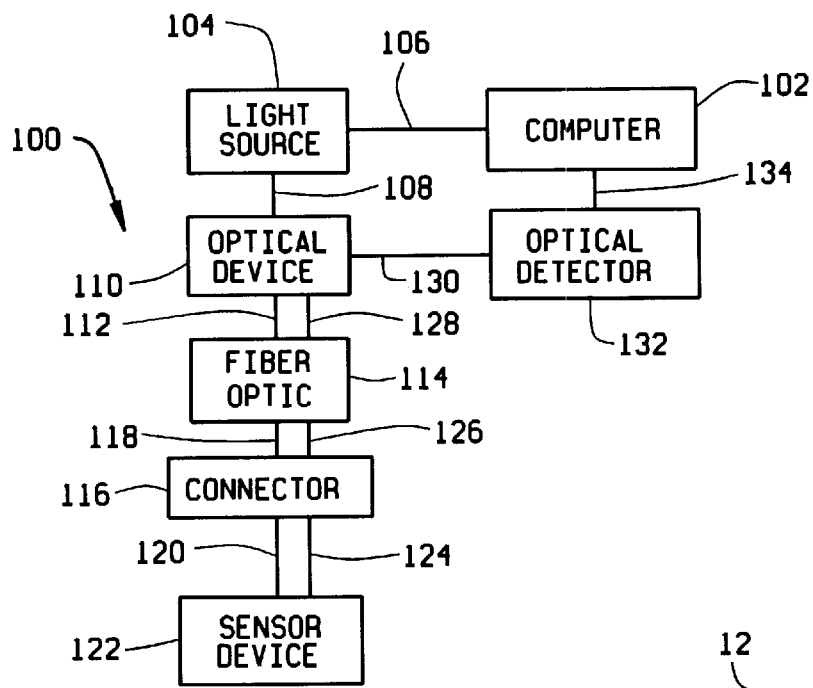
FIG. 5 is a block diagram of a second embodiment of the micro optical fiber sensor device constructed according to the present invention.

FIG. 5 illustrates another preferred embodiment of a sensor device 100 which comprises a computer 102 which is connected to a light source 104 by a wire 106. The light source 104 operates to provide light, represented by a light beam 108, to be projected at an optical device 110. The optical device 110 may be a mirror which allows light, which is represented by a light beam 112, of a particular or predetermined wavelength or frequency to pass through the device 110 to be directed at a fiber optic 114. The fiber optic 114 is connected to a connector device 116 and the fiber optic 114 passes light, such as light beam 118, through to the connector device 116. A beam of light 120 is transmitted from the connector device 116 to a sensor device 122. The sensor device 122 is similar to the tip portion or device 38 which was shown in FIGS. 2 and 3. Light, such as light beam 124, which may be reflected back from a sample (not shown) and through the sensor device 122, is directed to the connector device 116. A light beam 126 is transmitted from the connector device 116 to the fiber optic 114. The fiber optic 114 in turn directs a light beam 128 to the optical device 110. The optical device 110 provides a light beam 130 of a particular or predetermined wavelength or frequency to be directed at an optical detector device 132. The optical detector 132 is connected by a wire 134 to the computer 102 and provides signals to the computer 102. The computer 102 is operatively programmed to use the signals provided from the optical detector 132 to calculate or determine the concentration of a substance within a sample.

Figure 6:
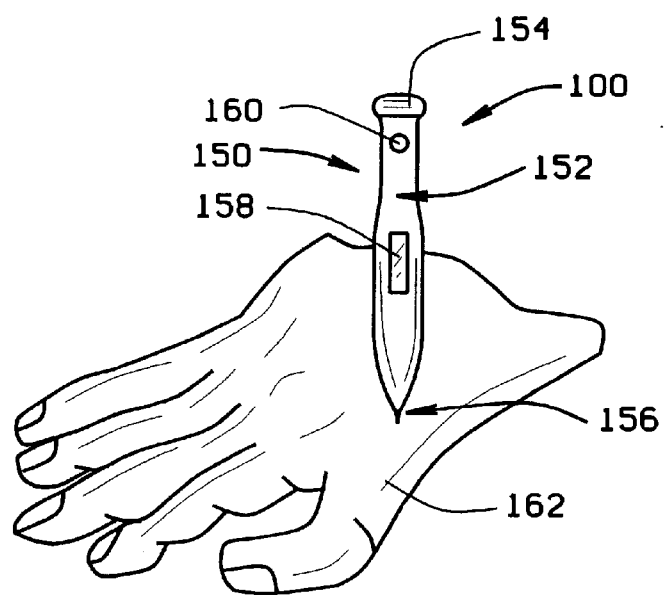
FIG. 6 is perspective view of the sensor device of FIG. 5 illustrated monitoring a concentration of glucose in a hand of a patient.

Referring now to FIG. 6, the sensor device 100 is further shown comprising a pencil like body 150 which includes a central body portion 152, an end cap 154, and a tip portion 156. The central body portion 152 has a display 158 for displaying information such as glucose concentration. An ON/OFF switch 160 is also included in the central body portion 152 for controlling operation of the sensor device 100. The sensor device 100 is illustrated having the tip portion 156 inserted into a hand 162 of a patient. As has been previously discussed, the tip portion 156 is of an extremely small size and because of its small size insertion of the tip portion 156 into the hand 162 will produce little or no sensation. The other components of the sensor device 100, which were discussed with reference to FIG. 5, are all housed within the central body portion 152.

With particular reference now to FIGS. 5 and 6, in operation, the tip portion 156 of the sensor device 100 is inserted into a sample, such as the hand 162, to detect the presence of a concentration of material, such as for example glucose. Once inserted into the hand 162, the ON/OFF switch 160 is pressed by the user to initiate operation of the sensor device 100. Actuation of the sensor device 100 causes the computer 102 to operate the light source 104. The light beam 108 is sent to the optical device 110 which causes the light beam 112 to be directed at the fiber optic 114 which in turn produces the light beam 118. The light beam 118 passes into the connector 116 and emerges as the light beam 120 which is provided to the sensor device 122. With the sensor device 122 being in contact with the hand 162, the sensor device 122 reacts chemically with the hand 162 and the color of the chemical composing the sensor device 122 changes. The color of the light beam 124 which is reflected back into the sensor device 122 is then directed back into the connector 116. The beam of light 126 is transmitted from the connector 116 to the fiber optic 114 which in turn transmits the beam of light 128 to the optical device 110. The optical device allows the light beam 130 to be directed to the optical detector 134. The optical detector 134 provides signals to the computer 102 which then determines the concentration of glucose within the hand 162. The result may then be displayed in the display 158 of the sensor device 100. Once the result is displayed, the user may remove the sensor device 100 from the hand 162 and press the ON/OFF switch 160 to turn the sensor device 100 off. The sensor device 100 may be used again to determine the glucose concentration.

The sensor device 100 in actual construction is a small device and sized and shaped to be pencil like. Because of its small size the sensor device 100 may be used as a portable monitoring device. Additionally, the computer 102 may be a microprocessor chip, a customized integrated circuit chip such as an ASIC chip, or any other device which is capable of processing electrical signals. Although not shown or made reference to, a rechargeable battery or a replaceable battery may be used to power the sensor device 100. Further both devices 10 and 100 may have incorporated therein a memory for storing information such as, for example, a log of monitoring of the patient's glucose concentration, time of day of monitoring, and date of monitoring.

Figure 7:
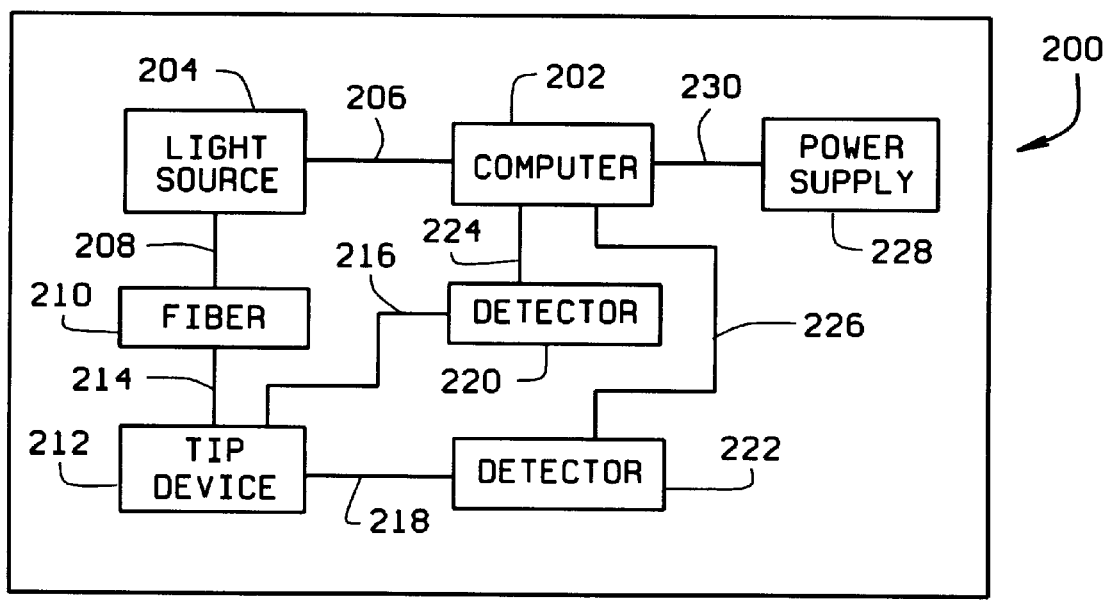
FIG. 7 is a block diagram of a third embodiment of the micro optical fiber sensor device constructed according to the present invention.

FIG. 7 depicts a block diagram of a third embodiment of a micro optical fiber sensor device 200. The sensor device 200 comprises a computer 202 which is connected to a light source 204 via a wire 206. The light source 204 projects a beam of light 208 into a section or portion of a fiber optic 210. The fiber optic 210 is connected to a tip portion or device 212 and passes a beam of light 214 to the tip device 212. The tip portion or device 212 is similar in several respects to the tip device 38 which was illustrated in FIGS. 2 and 3, however, the tip device 212 is different in one respect. In fabricating the tip device 212, as discussed in U.S. Pat. Nos. 5,361,314 and 5,627,922, the tip device 212 uses a multi-dye matrix tip which is photochemically attached to the tip device 212 to form a multi-functional sensor having an extremely small size. The multi-dye configuration allows for a multi-function sensor in which each dye may be chemically activated by a different chemical compound. This enables the tip device 212 to sense, detect, or monitor more than one chemical.

Since the tip device 212 is capable of monitoring two different chemicals, two different light beams, such as light beams 216 and 218, will be reflected back from a sample and through the tip device 212. Each of the light beams 216 and 218 are directed to a detector 220 and 222, respectively. Although not shown, it is possible to have an optical component, such as band pass filters, placed between the tip device 212 and the detectors 220 and 222 to direct the light beams 216 and 218 to a specific detector 220 or 222. The detector 220 is connected to the computer 202 by a wire 224 and electrical signals indicative of the concentration of a particular chemical within a sample is provided to the computer 202. Additionally, the detector 222 is connected to the computer 202 by another wire 226 and signals indicative of another chemical within the sample are provided to the computer 202. In this manner, the computer 202 is programmed to receive the signals from the detectors 220 and 222 and calculate or determine the concentrations of the two chemicals within the sample. Additionally, the sensor device 200 may include a display (not shown) which would display the results of the calculations. The sensor device 200 may also be provided with a power supply 228 which is operatively connected by a wire 230 to the computer 202. Although the device 200 is depicted to show the monitoring of at least two different chemical compounds it is also contemplated that more than two chemical compounds may be sensed, detected, or monitored by the device 200 by adding additional components, as has been taught and illustrated.

From all that has been said, it will be clear that there has thus been shown and described herein a micro optical fiber sensor device which fulfills the various objects and advantages sought therefor. It will be apparent to those skilled in the art, however, that many changes, modifications, variations, and other uses and applications of the subject micro optical fiber sensor device are possible and contemplated. All changes, modifications, variations, and other uses and applications which do not depart from the spirit and scope of the invention are deemed to be covered by the invention, which is limited only by the claims which follow.

What is claimed is:

1. A sensor device for measuring a concentration of a substance within a sample comprising:

a sensor comprising an optical fiber portion having a first end and a second end, the second end having a tip portion attached thereto and an active material incorporated within the tip portion, the tip portion adapted to be inserted into a sample, the active material capable of interacting with a substance within a sample;

a light source coupled to the first end of the sensor for emitting a beam of light into and through the sensor and into a sample, the emitted beam of light having a wavelength and the active material interacting with a substance within a sample to change the wavelength of the emitted beam of light to produce a reflected beam of light and the sensor for transmitting the reflected beam of light out of the second end thereof;

means for receiving the reflected beam of light from the second end of the sensor for producing a signal indicative of the reflected beam of light; and a processor for receiving the signal indicative of the reflected beam of light and for processing the signal to determine the concentration of a substance within a sample.

2. The sensor device of claim 1 wherein the active material is preselected to interact with a predetermined substance within a sample.

3. The sensor device of claim 1 wherein the reflected beam of light has a wavelength which is different from the wavelength of the emitted beam of light.

4. The sensor device of claim 1 wherein the receiving means is an optical detector.

5. The sensor device of claim 1 wherein the concentration to be measured is glucose and the sample is a human.

6. The sensor device of claim 1 further comprising a pencil shaped and sized body having a tip portion, a central body, and an end cap.

7. The sensor device of claim 1 wherein the tip portion comprises a biologically active compound that is immobilized in an environment that is optically reactive.

8. A sensor device for measuring a concentration of a substance within a sample comprising:

a sensor comprising an optical fiber portion having a first end and a second end, the second end having a tip portion attached thereto and an active material incorporated within the tip portion, the tip portion adapted to be inserted into a sample, the active material capable of interacting with a substance within a sample;

a light source for emitting a beam of light of a preselected wavelength with the light source being coupled to an optical device capable of transmitting the beam of light therethrough, the transmitted beam of light being directed into the first end of the sensor, through the sensor, and out of the second end into a sample, the active material interacting with a substance within a sample to change the wavelength of the transmitted beam of light to produce a reflected beam of light and the sensor for transmitting the reflected beam of light from the second end, through the sensor, and out of the first end thereof, the optical device being further capable of reflecting the reflected beam of light;

means for receiving the reflected beam of light which is reflected by the optical device for producing a signal indicative of the reflected beam of light; and a processor for receiving the signal indicative of the reflected beam of light and for processing the signal to determine the concentration of a substance within a sample.

9. The sensor device of claim 8 wherein the active material is preselected to interact with a predetermined substance within a sample.

10. The sensor device of claim 8 wherein the reflected beam of light has a wavelength which is different from the wavelength of the transmitted beam of light.

11. The sensor device of claim 8 wherein the receiving means is an optical detector.

12. The sensor device of claim 8 wherein the concentration to be measured is glucose and the sample is a human.

13. The sensor device of claim 8 further comprising a pencil shaped and sized body having a tip portion, a central body, and an end cap.

14. The sensor device of claim 8 wherein the tip portion comprises a biologically active compound that is immobilized in an environment that is optically reactive.

15. A sensor device for measuring a concentration of a substance within a sample comprising:
- a sensor comprising an optical fiber portion having a first end and a second end, the second end having a tip portion attached thereto and a first and a second active material incorporated within the tip portion, the tip portion adapted to be inserted into a sample, the first active material capable of interacting with a first substance within a sample and the second active material capable of interacting with a second substance within a sample;
- a light source coupled to the first end of the sensor for emitting a beam of light into and through the sensor and into a sample, the emitted beam of light having a wavelength and the first active material interacting with a first substance within a sample to change the wavelength of the emitted beam of light to produce a first reflected beam of light, the second active material interacting with a second substance within a sample to change the wavelength of the emitted beam of light to produce a second reflected beam of light, and the sensor for transmitting the first and second reflected beams of light out of the second end thereof;
- means for receiving the first and second reflected beams of light from the second end of the sensor for producing a first signal indicative of the first reflected beam of light and a second signal indicative of the second reflected beam of light; and
- a processor for receiving the first and second signals and for processing the first and second signals to determine the concentration of a first substance within a sample and the concentration of a second substance with a sample.

16. The sensor device of claim 15 wherein the receiving means comprises a first means for receiving the first reflected beam of light and a second means for receiving the second beam of light.

17. The sensor device of claim 16 wherein the first means for receiving is an optical detector and the second means for receiving is an optical detector.

18. The sensor device of claim 15 wherein the first concentration to be measured is glucose and the sample is a human.

19. The sensor device of claim 15 further comprising a pencil shaped and sized body having a tip portion, a central body, and an end cap.

20. The sensor device of claim 15 wherein the tip portion comprises a biologically active compound that is immobilized in an environment that is optically reactive.

* * * * *